Sept. 21, 1926. Re. 16,425

J. BIRD

CARBON REMOVING ATTACHMENT FOR INTERNAL COMBUSTION ENGINES

Original Filed June 24, 1924

INVENTOR
JOHN BIRD
BY
Mason, Fenwick & Lawrence
ATTORNEY

Reissued Sept. 21, 1926. Re. 16,425

UNITED STATES PATENT OFFICE.

JOHN BIRD, OF CAMDEN, MAINE.

CARBON-REMOVING ATTACHMENT FOR INTERNAL-COMBUSTION ENGINES.

Original No. 1,565,778, dated December 15, 1925, Serial No. 722,098, filed June 24, 1924. Application for reissue filed January 12, 1926. Serial No. 80,842.

This invention relates to a combination with an internal combustion engine of a hollow cylindrical chamber adapted to contain a chemical element, and more particularly to improvements in the means at the outer end of the chamber for admitting air to the chamber which will circulate freely with the chemical element when the engine is in operation.

Other objects will appear as the description proceeds.

Figure 1:
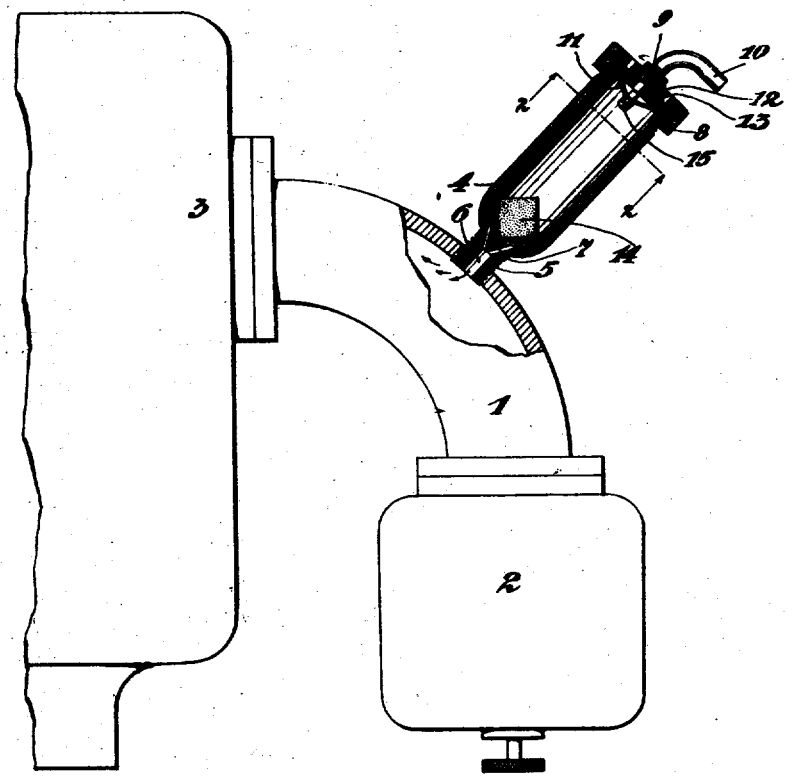
Figure 2:
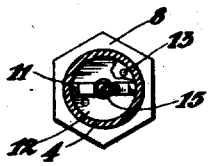

Figure 1 is an end elevation of a portion of an internal combustion engine intake manifold and carburetor, showing my improved carbon removing attachment in section, as applied to the said intake manifold, and Figure 2 is a transverse sectional view taken on the line 2—2 of Figure 1.

Like characters of reference are used throughout the following specification and the accompanying drawings to designate corresponding parts.

My improved carbon removing attachment is applied to the intake manifold 1, which is connected beteen the carburetor 2 and internal combustion engine 3, and comprises a cylindrical housing 4, which is slightly restricted at its lower end and terminates in a threaded end or shank portion 5, where it threads into the said intake manifold 1. The lower portion of the shank 5 is formed with an internal passage 6, and is connected wtih the interior of the housing 4 by means of the outwardly flared passages 7.

The lower or inner end of the chambered housing is adapted to retain the chemical 4 preferably by being formed with a pocket in its bottom to hold the same which pocket is surrounded by the series of small gas passages 7 leading downward into the manifold, so that when the chemical disintegrates it will be retained in the pocket and will not be drawn with the gases into the manifold.

The outer end of the housing is externally threaded and is adapted to receive the removable threaded cap member 8, which is provided at its center portion with a threaded stem 9, which terminates at its outer end with a handle portion 10, and carries at its inner end a removable spring member 11, which is adjustably tensions the valve or washer 12 against the under surface of the cap member 8. A plurality of ports 13 are formed through the cap member 8 and are normally closed when the engine is idle by means of the valve or washer 12.

From the foregoing description it will be apparent that when the internal combustion engine is started, the suction in the intake manifold will draw the valve or washer 12 down against the spring member 11, so that the ports 13 will be uncovered and the air will be drawn therethrough and over the chemical, and through the passages 7 and 6 and in through the intake manifold to the interior of the engine 3, where the chemicalized air will cut and clean the carbon deposits. It will be noted that the valve or washer 12 is slightly smaller in diameter than the inner diameter of the housing 4, thereby making it possible for the air to be drawn around the same as it passes over the chemical and into the engine.

It will be readily understood that the tension on the spring member 11 may be adjusted, as desired, by simply turning up or down on the threaded stem 9. If perchance the spring member 11 should become broken or in any manner injured, the new member may readily be placed in position by removing the screw 15 and replacing the new member.

Owing to the self-closing air admission valve being located in advance of the chemical element in the mixing chamber instead of between the chemical element and the intake manifold, the air is automatically shut off from the chamber and the volatile chemical element when the motor is idle, so that vaporization and waste of the volatile chemical element is prevented, and when the motor is running, owing to the natural expansion of the air as it is admitted into the mixing chamber through the restricted part of the valve, a more perfect mixture of the air with the chemical vapor is obtained.

My improved attachment may also be applied to the mixing chamber in a carbureter with equally good results.

Many minor changes in detail of construction may be resorted to without departure from the spirit of the invention.

For example, the air valve need not be self-closing but may be closed or adjusted by hand, and the valve need not be wholly closed when the motor is idle, but merely closed to an extent necessary to prevent appreciable vaporization and waste of the chemical.

Having thus described my invention what I claim as new and desire to secure by Letters Patent of the United States is:

1. In combination, a hollow cylindrical chamber adapted to contain a chemical element, of means at the outer end of the chamber adapted to admit air over the chemical element, the said means comprising a removable threaded cap member, which is provided at its center portion with a threaded stem, and carries on its inner end a removable spring member, and a valve member disposed between the spring and the cap whereby the valve element may be adjustably tensioned against the under surface of the cap member.

2. In combination, a hollow cylindrical chamber adapted to contain a chemical element, of means at the outer end of the chamber adapted to admit air over the chemical element, the said means comprising a removable threaded cap member having air admitting ports and which is provided at its center portion with a threaded stem, terminating at its outer end in a handle, and carrying on its inner end a removable spring member, a valve member disposed between the spring and the cap whereby the valve element may be adjustably tensioned against the under surface of the cap member.

3. An attachment for gasoline engines comprising a tubular member exteriorly threaded adjacent each end, the bore of said body restricted at one end and said restricted bore communicating with the main bore by a plurality of small flaring passages communicating with the main bore about its periphery, a closure cap adapted to engage the threads on the other end of the body, said cap having air inlet ports and a centrally located stem in threaded engagement with the cap, a disk adapted to seat over said stem and against the inner face of the cap and spring mounted on the inner end of the stem to resiliently force the disk to its seat substantially as specified.

4. An attachment for internal combustion motors, consisting of a chamber provided at its inner end with means to hold and retain a volatile chemical element and with an air passage leading into the motor, and an air valve at the outer end of the chamber to admit air through the chamber and around the chemical to the motor when the motor is running and to exclude the air from the chemical when the motor is idle to an extent necessary to prevent vaporization and waste of the chemical.

5. An attachment for internal combustion motors, consisting of a chamber provided at its inner end with a pocket to hold and retain a volatile chemical element and with air passages around said pocket leading into the motor, and an air valve at the outer end of the chamber to admit air through the chamber and around the chemical to the motor when the motor is running and to exclude the air from the chemical when the motor is idle to an extent necessary to prevent vaporization and waste of the chemical.

In testimony whereof I affix my signature.

JOHN BIRD.